US008219366B2

(12) United States Patent
Titz et al.

(10) Patent No.: US 8,219,366 B2
(45) Date of Patent: Jul. 10, 2012

(54) DETERMINATION OF ELBOW VALUES FOR PCR FOR PARABOLIC SHAPED CURVES

(75) Inventors: Martin Titz, Rotkreuz (CH); Ronald T. Kurnik, Foster City, CA (US)

(73) Assignee: Roche Molecular Sytems, Inc., Pleasanton, CA (US)

( * ) Notice: Subject to any disclaimer, the term of this patent is extended or adjusted under 35 U.S.C. 154(b) by 505 days.

(21) Appl. No.: 12/548,353

(22) Filed: Aug. 26, 2009

(65) Prior Publication Data

US 2011/0054852 A1 Mar. 3, 2011

(51) Int. Cl.
*G06F 17/10* (2006.01)
(52) U.S. Cl. ............................................... 703/2; 702/19
(58) Field of Classification Search .................. 703/2, 6, 703/11; 702/19
See application file for complete search history.

(56) References Cited

U.S. PATENT DOCUMENTS

| 5,373,457 | A  | * | 12/1994 | George et al. ...................... 703/2 |
| 7,668,663 | B2 |   | 2/2010  | Kurnik et al. |
| 7,680,604 | B2 | * | 3/2010  | Kurnik ............................. 702/19 |
| 7,680,868 | B2 |   | 3/2010  | Kurnik et al. |
| 7,788,039 | B2 | * | 8/2010  | Vess ................................ 702/19 |
| 7,991,561 | B2 | * | 8/2011  | Kurnik ............................. 702/19 |
| 7,991,562 | B2 | * | 8/2011  | Kurnik et al. .................... 702/19 |
| 2006/0009916 | A1 | * | 1/2006 | Li et al. ............................ 702/20 |
| 2007/0143070 | A1 |   | 6/2007  | Kurnik et al. |
| 2008/0033701 | A1 |   | 2/2008  | Kurnik |
| 2009/0119020 | A1 |   | 5/2009  | Kurnik et al. |
| 2009/0287754 | A1 | * | 11/2009 | Sane et al. ..................... 708/270 |
| 2010/0070185 | A1 |   | 3/2010  | Kurnik et al. |

FOREIGN PATENT DOCUMENTS

| WO | WO 97/46707 A2 | 12/1997 |
| WO | WO 97/46707 A3 | 12/1997 |
| WO | WO 97/46712 A2 | 12/1997 |
| WO | WO 97/46712 A3 | 12/1997 |
| WO | WO 97/46714 A1 | 12/1997 |

OTHER PUBLICATIONS

Chandrasekaran et al., "Summarizing data through a piecewise linear growth curve model", Statistics in Medicine, vol. 24, Issue 8, Apr. 2005, pp. 1139-1151.*
Lei et al., "Comparison and selection of growth models using the Schnute model", Journal of Forest Science, 52, 2006 (4), pp. 188-196.*
Cogger, "Piecewise Linear Modeling: Theory, Guidelines, and Applications", Management Science & Techlogy Symposium, University of Kansas School of Business, Mar. 2006.*
Hu, "Akaike Information Criterion", Center for Research in Scientific Computation, North Carolina State University, Mar. 2007, 19 pages.*

(Continued)

*Primary Examiner* — Kamini S Shah
*Assistant Examiner* — Herng-Der Day
(74) *Attorney, Agent, or Firm* — Kilpatrick Townsend & Stockton LLP (57) ABSTRACT

Systems and methods for processing PCR curves, and for identifying the presence of a parabolic-shaped PCR curve. Use of a piecewise linear approximation of a PCR curve enables a more realistic elbow value to be determined in the case of parabolic shaped PCR curves.

14 Claims, 4 Drawing Sheets

OTHER PUBLICATIONS

Bièche, I. et al., "Quantitation of *MYC* Gene Expression in Sporadic Breast Tumors with a Real-Time Reverse Transcription-PCR Assay," *Cancer Research*, Jun. 15, 1999, vol. 59, pp. 2759-2765.

Gibson, U.E.M. et al., "A Novel Method for Real Time Quantitative RT-PCR," *Genome Research*, 1996, vol. 6, pp. 995-1001.

Wang, S-S. et al., "Homogenous Real-Time Detection of Single-Nucleotide Polymorphisms by Strand Displacement Amplification on the BD ProbeTec ET System," *Clinical Chemistry*, 2003, vol. 49, No. 10, pp. 1599-1607.

Weusten, J.J.A.M. et al., "Principles of quantitation of viral loads using nucleic acid sequence-based amplification in combination with homogenous detection using molecular beacons," *Nucleic Acids Research*, 2002, vol. 30, No. 6, e26, pp. 1-7.

* cited by examiner

DETERMINATION OF ELBOW VALUES FOR PCR FOR PARABOLIC SHAPED CURVES

BACKGROUND

The present invention relates generally to systems and methods for processing Polymerase Chain Reaction (PCR) data, and more particularly to systems and methods for determining characteristic cycle threshold (Ct) or elbow values in PCR amplification curves, or elbow values in other growth curves, that have a parabolic shape.

The Polymerase Chain Reaction is an in vitro method for enzymatically synthesizing or amplifying defined nucleic acid sequences. The reaction typically uses two oligonucleotide primers that hybridize to opposite strands and flank a template or target DNA sequence that is to be amplified. Elongation of the primers is catalyzed by a heat-stable DNA polymerase. A repetitive series of cycles involving template denaturation, primer annealing, and extension of the annealed primers by the polymerase results in an exponential accumulation of a specific DNA fragment. Fluorescent probes or markers are typically used in the process to facilitate detection and quantification of the amplification process.

Figure 1:
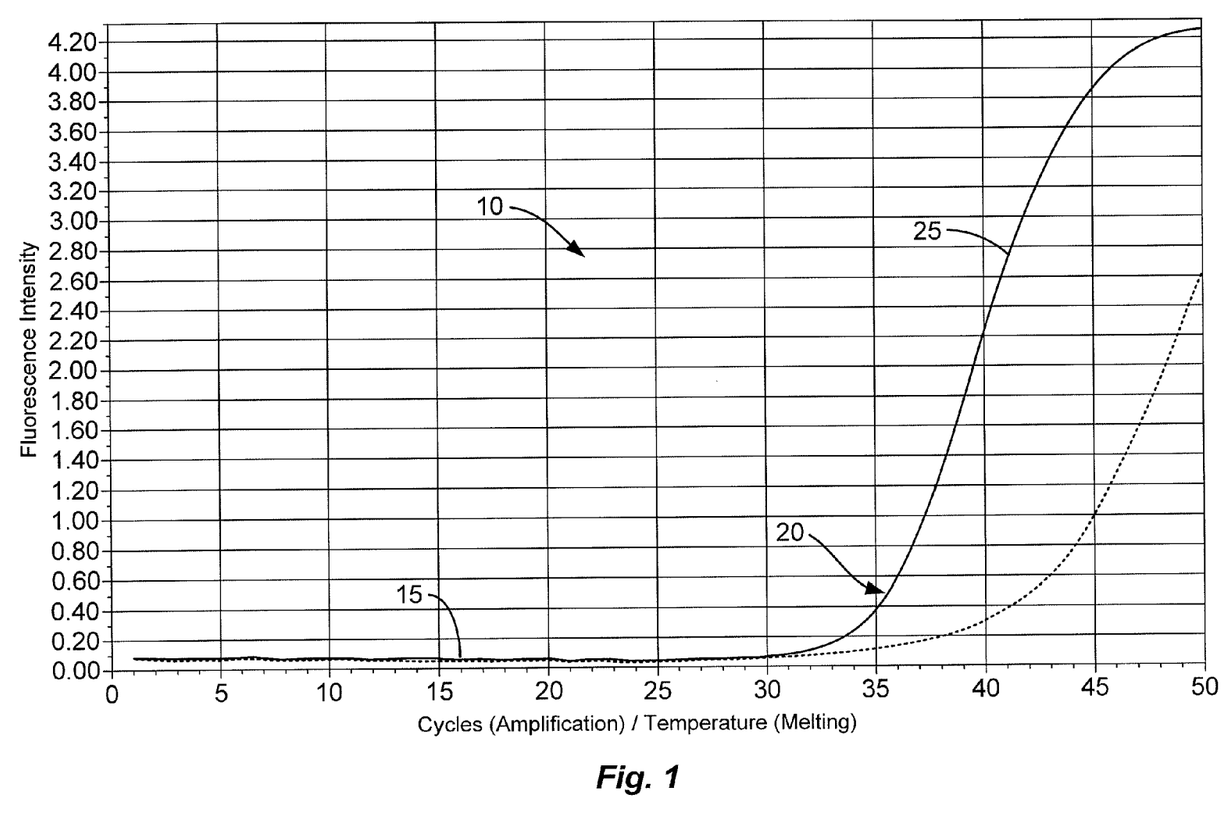
FIG. 1 illustrates a typical growth or amplification curve in the context of a PCR process having a sigmoidal shape (solid line) and a PCR curve having a parabolic shape (dotted line).

A typical real-time PCR curve is shown in FIG. 1 (solid line), where fluorescence intensity values are plotted vs. cycle number for a typical PCR process. In this case, the formation of PCR products is monitored in each cycle of the PCR process. The amplification is usually measured in thermocyclers which include components and devices for measuring fluorescence signals during the amplification reaction. An example of such a thermocycler is the Roche Diagnostics LightCycler (Cat. No. 20110468). The amplification products are, for example, detected by means of fluorescent labelled hybridization probes which only emit fluorescence signals when they are bound to the target nucleic acid or in certain cases also by means of fluorescent dyes that bind to double-stranded DNA.

For a typical PCR curve, identifying a transition point at the end of the baseline region, which is referred to commonly as the elbow value or cycle threshold (Ct) value, is extremely useful for understanding characteristics of the PCR amplification process. The Ct value may be used as a measure of efficiency of the PCR process. For example, typically a defined signal threshold is determined for all reactions to be analyzed and the number of cycles (Ct) required to reach this threshold value is determined for the target nucleic acid as well as for reference nucleic acids such as a standard or housekeeping gene. The absolute or relative copy numbers of the target molecule can be determined on the basis of the Ct values obtained for the target nucleic acid and the reference nucleic acid (Gibson et al., Genome Research 6:995-1001; Bieche et al., Cancer Research 59:2759-2765, 1999; WO 97/46707; WO 97/46712; WO 97/46714). The elbow value in region 20 at the end of the baseline region 15 in FIG. 1 would be in the region of cycle number 36.

The determination of elbows (or cycle thresholds, Ct) for PCR curves is needed for quantitative analysis of real-time PCR (RT-PCR). Many algorithms have been developed for this use, e.g., based on intersection of a normalized data curve with a threshold or by determining the maximum curvature or 2nd derivative, either analytically (e.g., using a curvature algorithm) or numerically, on a normalized data curve, as described in U.S. application Ser. No. 11/316,315, filed Dec. 20, 2005; U.S. application Ser. No. 11/349,550, filed Feb. 6, 2006; U.S. application Ser. No. 11/458,644, filed Jul. 19, 2006; U.S. application Ser. No. 11/533,291, filed Sep. 19, 2006; U.S. application Ser. No. 11/861,188, filed Sep. 25, 2007; U.S. application Ser. No. 12/209,912, filed Sep. 12, 2008 ("ELCA Algorithm"), the disclosures of which are each hereby incorporated by reference for all purposes. These methods work exceedingly well provided that the underlying curve approximates a sigmoid shape. In the rare occasion when the raw data curve has a parabolic shape, then the elbow value as determined by these methods will typically result in an elbow value that is larger than one would expect by examination of the data curve.

Consider the real-time PCR (RT-PCR) curves from a West Nile Virus (WNV) assay shown in FIG. 1. The solid black curve has a typical sigmoidal shape, which is amendable to analysis with algorithms developed previously. The dashed curve, however, resembles a parabolic curve and lacks a plateau region. The elbow values of the two curves shown in FIG. 1 have the values given in Table 1 below, when analyzed by the ELCA Algorithm as an example. The ELCA Algorithm numerically determines the elbow value as the point of maximum in the curvature or second derivative.

TABLE 1

| Ct values for Sigmoidal and Parabolic Curves | |
|---|---|
| | ELCA Ct |
| Solid Curve | 35.46 |
| Dashed Curve | 45.43 |

The elbow value for the solid curve is consistent with the value one would normally assign to a sigmoid curve, whereas a vertical line drawn at the elbow value for the parabolic dashed curve intersects the dashed curve at a value significantly higher than one would typically assign to this curve.

Accordingly, it is desirable to develop systems and methods to deal with these type of curves, and also to identify when such a parabolic curve is present.

BRIEF SUMMARY

The present invention provides systems and methods to process PCR curves, and to identify the presence of a parabolic-shaped PCR curve. According to one embodiment, use of a piecewise linear approximation of a PCR curve enables a more realistic elbow value to be determined in the case of parabolic shaped PCR curves.

According to one aspect of the present invention, a computer-implemented method of determining a Ct value for a real-time PCR data curve having a parabolic shape is provided. The method typically includes steps that are implemented in a processor of a computer system or other device or machine, and which include receiving a data set representing a PCR growth curve, the data set having a plurality of coordinate values (x,y), and approximating the data set using a two segment piecewise linear function having a first linear segment ending at x* and a second linear segment beginning at x*. The method also typically includes the steps of determining whether the PCR growth curve has a parabolic shape by determining: a) whether an $R^2$ value of a quadratic fit to the data points beginning with x* to the end of the data set is above a predetermined threshold value, wherein the threshold value is 0.90 or above; and b) whether an $R^2$ value of the two segment piecewise fit over substantially all the data set is above a threshold value of 0.85 or above; and c) determining whether the slope of the second segment is greater than the slope of the first segment if both slopes are greater than zero; and if so, estimating the Ct value of the data set by determining the intersection of the second linear segment with a baseline subtracted horizontal line. The method also typically includes the step of outputting the Ct value for display or further processing.

According to another aspect of the present invention, a tangible computer readable medium is provided that stores code for controlling a processor to determine a Ct value for a real-time PCR data curve having a parabolic shape. The code typically includes instructions, which when executed by a processor, cause the processor to receive a data set representing a PCR growth curve, the data set having a plurality of coordinate values (x,y), and to approximate the data set using a two segment piecewise linear function having a first linear segment ending at x* and a second linear segment beginning at x*. The code also typically includes instructions to determine whether the PCR curve has a parabolic shape. In certain aspects, this determination is done by determining (a) whether an $R^2$ value of a quadratic fit to the data points beginning with x* to the end of the data set is above a threshold value of 0.90 or above; and (b) whether an $R^2$ value of the two segment piecewise fit over substantially all the data set is above a threshold value of 0.85 or above; and (c) whether the slope of the second segment is greater than the slope of the first segment if both slopes are greater than zero. The code also typically include instructions to estimate the Ct value of the data set by determining the intersection of the second linear segment with a mean value of a baseline subtracted horizontal line if (a), (b) and (c) are true, and to output the Ct value for display or further processing.

According to yet another aspect of the present invention, a real-time Polymerase Chain Reaction (PCR) system is provided that typically includes a PCR analysis module that generates a PCR data set representing a PCR amplification curve, the data set including a plurality of data points each having a pair of coordinate values (x,y), wherein the data set includes data points in a region of interest which includes a cycle threshold (Ct) value, and an intelligence module adapted to process the PCR data set to determine the Ct value. The Ct value is typically determined by approximating the data set using a two segment piecewise linear function having a first linear segment ending at x* and a second linear segment beginning at x*, and determining whether the PCR growth curve has a parabolic shape. Determining whether the curve has a parabolic shape is typically done by a) determining whether an $R^2$ value of a quadratic fit to the data points beginning with x* to the end of the data set is above a threshold value of 0.90 or above, and b) determining whether an $R^2$ value of the two segment piecewise fit over substantially all the data set is above a threshold value of 0.85 or above, and c) determining whether the slope of the second segment is greater than the slope of the first segment if both slopes are greater than zero, and if a), b), and c) are true, then estimating the Ct value of the data set by determining the intersection of the second linear segment with a baseline subtracted horizontal line, and outputting the Ct value for display or further processing.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

DETAILED DESCRIPTION OF THE INVENTION

The present invention provides systems and methods for identifying parabolic-shaped PCR curves and for processing such curves to determine Ct values.

One example of a typical growth or amplification curve 10 in the context of a PCR process having a sigmoidal shape is shown in FIG. 1 as a solid curve. As shown, the curve 10 includes a lag phase region 15, and an exponential phase region 25. Lag phase region 15 is commonly referred to as the baseline or baseline region. Such a curve 10 includes a transitionary region of interest 20 linking the lag phase and the exponential phase regions. Region 20 is commonly referred to as the elbow or elbow region. The elbow region typically defines an end to the baseline and a transition in the growth or amplification rate of the underlying process. Identifying a specific transition point in region 20 can be useful for analyzing the behavior of the underlying process. In a typical PCR curve, identifying a transition point referred to as the elbow value or cycle threshold (Ct) value is useful for understanding qualitative and quantitative characteristics of the PCR process. For example, the Ct value can be used to provide quantization of the amount of DNA present in the sample being analyzed. Quantization is obtained by performing a calibration curve of the Log(DNA Amount) vs. Ct value. Subsequent samples can then use Ct values along with the calibration curve to directly obtain estimates of DNA in a sample. Ct values can also be used to provide qualitative information on the DNA sample.

Other processes that may provide similar curves having a parabolic shape without a plateau region include bacterial processes, enzymatic processes and binding processes. In bacterial growth curves, for example, the transition point of interest has been referred to as the time in lag phase, λ. Other specific processes that produce data curves that may be analyzed according to the present invention include strand displacement amplification (SDA) processes, nucleic acid sequence-based amplification (NASBA) processes and transcription mediated amplification (TMA) processes. Examples of SDA and NASBA processes and data curves can be found in Wang, Sha-Sha, et al., "Homogeneous Real-Time Detection of Single-Nucleotide Polymorphisms by Strand Displacement Amplification on the BD ProbeTec ET System," Clin Chem 2003 49 (10):1599, and Weusten, Jos J. A. M., et al., "Principles of Quantitation of Viral Loads Using Nucleic Acid Sequence-Based Amplification in Combination With Homogeneous Detection Using Molecular Beacons," Nucleic Acids Research, 2002 30(6):26, respectively, both of which are hereby incorporated by reference. Thus, although the remainder of this document will discuss embodiments and aspects of the invention in terms of its applicability to PCR curves, it should be appreciated that the present invention may be applied to data curves related to other processes.

As shown in FIG. 1, data for a typical PCR growth curve can be represented in a two-dimensional coordinate system, for example, with PCR cycle number defining the x-axis and an indicator of accumulated polynucleotide growth defining the y-axis. Typically, the indicator of accumulated growth is a fluorescence intensity value as the use of fluorescent markers is perhaps the most widely used labeling scheme. However, it should be understood that other indicators may be used depending on the particular labeling and/or detection scheme used. Examples of other useful indicators of accumulated signal growth include luminescence intensity, chemiluminescence intensity, bioluminescence intensity, phosphorescence intensity, charge transfer, voltage, current, power, energy, temperature, viscosity, light scatter, radioactive intensity, reflectivity, transmittance and absorbance. The definition of cycle can also include time, process cycles, unit operation cycles and reproductive cycles.

General Process Overview

Consider the Real-Time PCR growth curves as shown in FIG. 1. It is desired to obtain from FIG. 1 a number called the Ct or elbow value form each curve. Oftentimes, as shown, real data for a PCR curve results in a parabolic shaped curve for which standard Ct determination processes do not work well. As discussed above with reference to Table 1, the elbow value for the solid curve is consistent with the value one would normally assign to a sigmoid curve, whereas the elbow value for the parabolic dashed curve is significantly higher than one would typically assign to this curve.

Figure 4:
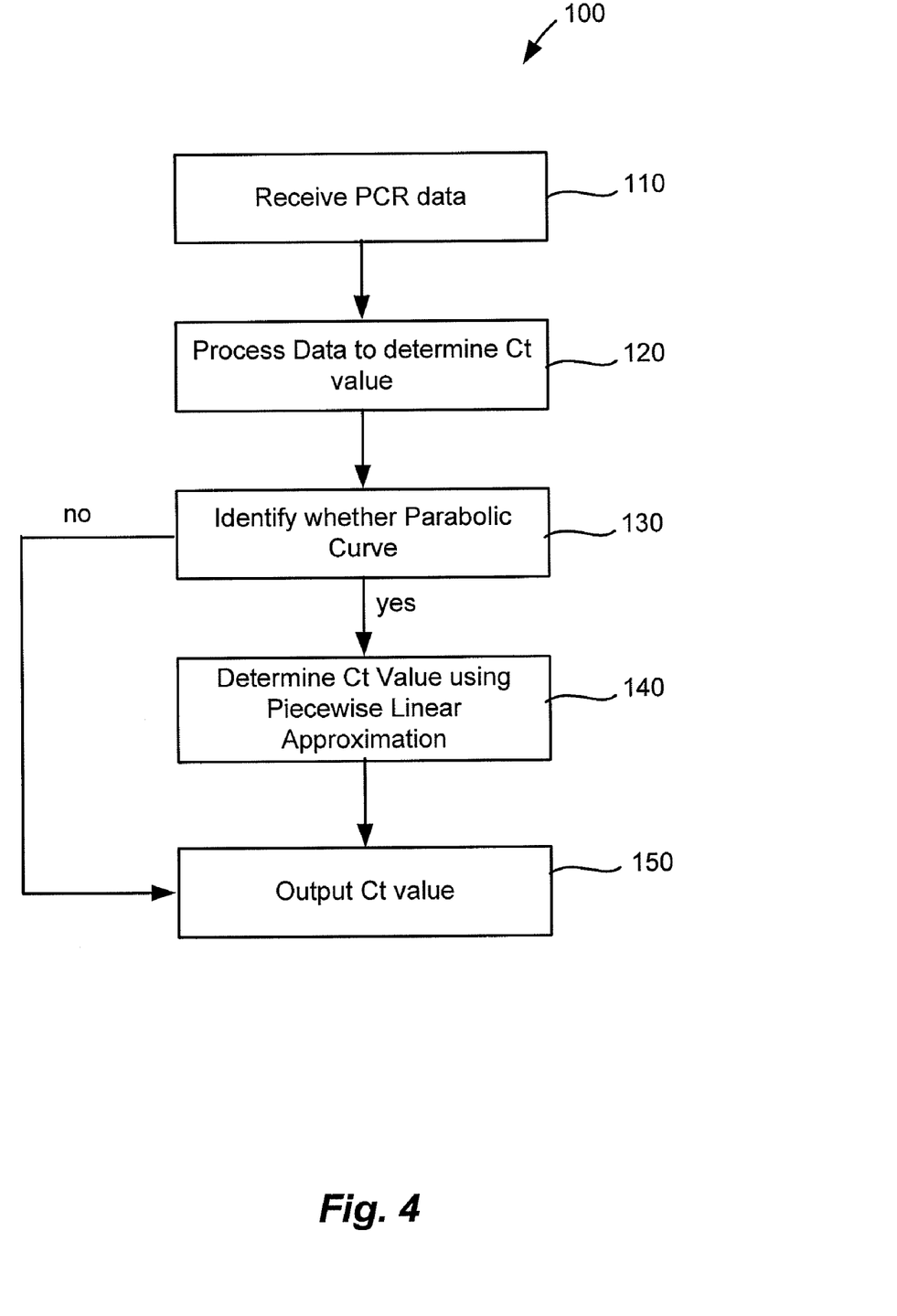
FIG. 4 illustrates a process for determining a transitionary value in a PCR curve according to one embodiment.

According to one embodiment, a process 100 for determining a transitionary value in a PCR curve, such as the elbow value or Ct value of a kinetic PCR amplification curve, can be described briefly with reference to FIG. 4. In step 110, an experimental data set representing the curve is received or otherwise acquired. An example of two plotted PCR data sets is shown in FIG. 1, where the y-axis and x-axis represent fluorescence intensity and cycle number, respectively, for a PCR curve. In certain aspects, the data set should include data that is continuous and equally spaced along an axis.

In the case where process 100 is implemented in an intelligence module (e.g., processor executing instructions) resident in a PCR data acquiring device such as a thermocycler, the data set may be provided to the intelligence module in real time as the data is being collected, or it may be stored in a memory unit or buffer and provided to the intelligence module after the experiment has been completed. Similarly, the data set may be provided to a separate system such as a desktop computer system or other computer system, via a network connection (e.g., LAN, VPN, intranet, Internet, etc.) or direct connection (e.g., USB or other direct wired or wireless connection) to the acquiring device, or provided on a portable medium such as a CD, DVD, floppy disk, memory stick or the like. In certain aspects, the data set includes data points having a pair of coordinate values (or a 2-dimensional vector). For PCR data, the pair of coordinate values typically represents the cycle number and the fluorescence intensity value. After the data set has been received or acquired in step 110, the data set may be analyzed to determine the end of the baseline region.

In step 120, the data set is processed according to a known process to determine a Ct value for the data set/curve. For example, the ELCA process may be used. In step 130, a determination is made as to whether the data set/curve has parabolic shape characteristics. In one embodiment, if all of the following conditions are satisfied, the data set/curve is determined to have parabolic characteristics and the Ct value is changed to that predicted by equation 4 as will be discussed below:

1. A quadratic fit to the data points beginning from x* until the end of the given data points is calculated. If the $R^2$ value of this fit is above a given threshold (default=0.90 or greater), the $C_T$ value is accepted. In one embodiment the threshold is set to 0.99.

2. A $R^2$ value of the piecewise linear fit vs. raw data (over all cycles)>threshold (default=0.85 or greater). In one embodiment the threshold is set to 0.95.

3. If a>0 and c>0, the ratio c/a is greater than a given threshold (default=1.1).

If it is determined that the data set/curve does exhibit parabolic characteristics, the process proceeds to step 140.

In step 140, the Ct value for a parabolic curve is determined. To define a more appropriate elbow value to the dashed curve (parabolic curve), a piecewise linear approximation to the RT-PCR curve is used in one embodiment. A piecewise linear function approximation of a parabolic curve according to one embodiment is given as follows:

Piecewise Linear Equation $$f(x) = \begin{cases} ax + b, & x \leq x^* \\ c(x - x^*) + ax^* + b, & x > x^* \end{cases} \quad \text{Equation 1}$$

Figure 2:
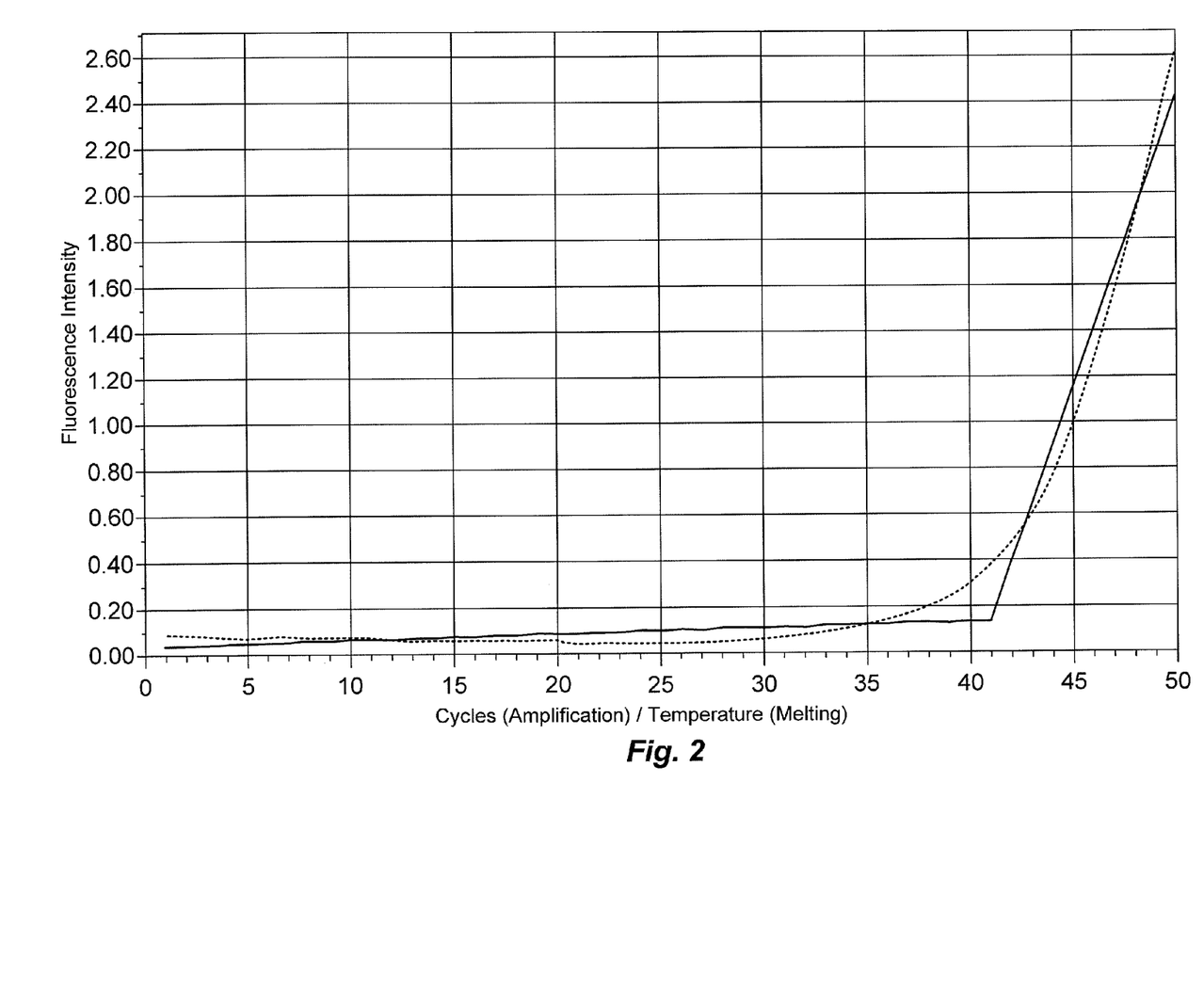
FIG. 2 illustrates a parabolic shaped PCR curve and a piecewise linear approximation.

In this equation, the piecewise linear function includes two linear functions joined at a common point, x*. The application of equation 1 is illustrated in FIG. 2, where both the parabolic curve and the piecewise linear approximation are shown.

In one embodiment, the piecewise linear curve is determined by minimization of the objective function shown in Equation 2 at a given value of x*.

Objective Function to Minimize $$E(a, b, c) = \frac{1}{2} \sum_{x_i \leq x^*} (ax_i + b - y_i)^2 + \frac{1}{2} \sum_{x_i > x^*} (c(x_i - x^*) + ax^* + b - y_i)^2 \quad \text{Equation 2}$$

To determine which value of x* to use in equation 2, in one embodiment the objective function is applied to all data points from cycles $x^* = n_0 \ldots n-1$. In theory $n_0$ can be defined as cycle 1 or cycle 2 or cycle 3, etc., however, to help reduce processing resource consumption, $n_0$ is set at about cycle 20 or 25 or so as these cycle values typically come before the end of the baseline region. The value of x* which has the minimum Akaike information coefficient (AIC) is chosen. The Akaike information coefficient is defined by:

Akaike Information Coefficient $$aic = n \cdot \ln\left(\frac{\|\hat{y} - y\|^2}{n}\right) + 2 \cdot m + \frac{2 \cdot m \cdot (m+1)}{n - m - 1}, \quad \text{Equation 3}$$

where m is the degrees of the freedom of the model, n is the length of the data set, y is the data vector and ŷ is the predicted model vector. Once the piecewise linear function has been determined, the Ct value is estimated as the intersection of the $2^{nd}$ part of the piecewise linear function with a horizontal line drawn at the mean value of the baseline subtracted raw data curve. Mathematically, this works out as:

Ct value for Parabolic Curves $$C_T = x^* + \frac{\underset{i=1...x^*}{\text{mean}} (y_i - ax_i - b)}{c - a}$$  Equation 4

In step 150, the Ct value as determined by equation 4 is output or returned, e.g., for display or further processing. Graphical displays may be rendered with a display device, such as a monitor screen or printer, coupled with the system that performed the analysis of FIG. 4, or data may be provided to a separate system for rendering on a display device. However, if, in step 130 it is determined that the data set/curve does not exhibit parabolic characteristics, the Ct value as determined by the process used in step 120 is output in step 150. It should be appreciated that both Ct values could be output if desired. Also, in certain embodiments, for example under the condition that the curve being processed has no plateau, the parabolic Ct determination process of equation 4 could be used as a stand alone algorithm rather than being a subset of another algorithm, such as ELCA, as discussed above (e.g., step 120 of FIG. 4 is omitted).

EXAMPLE

Figure 3:
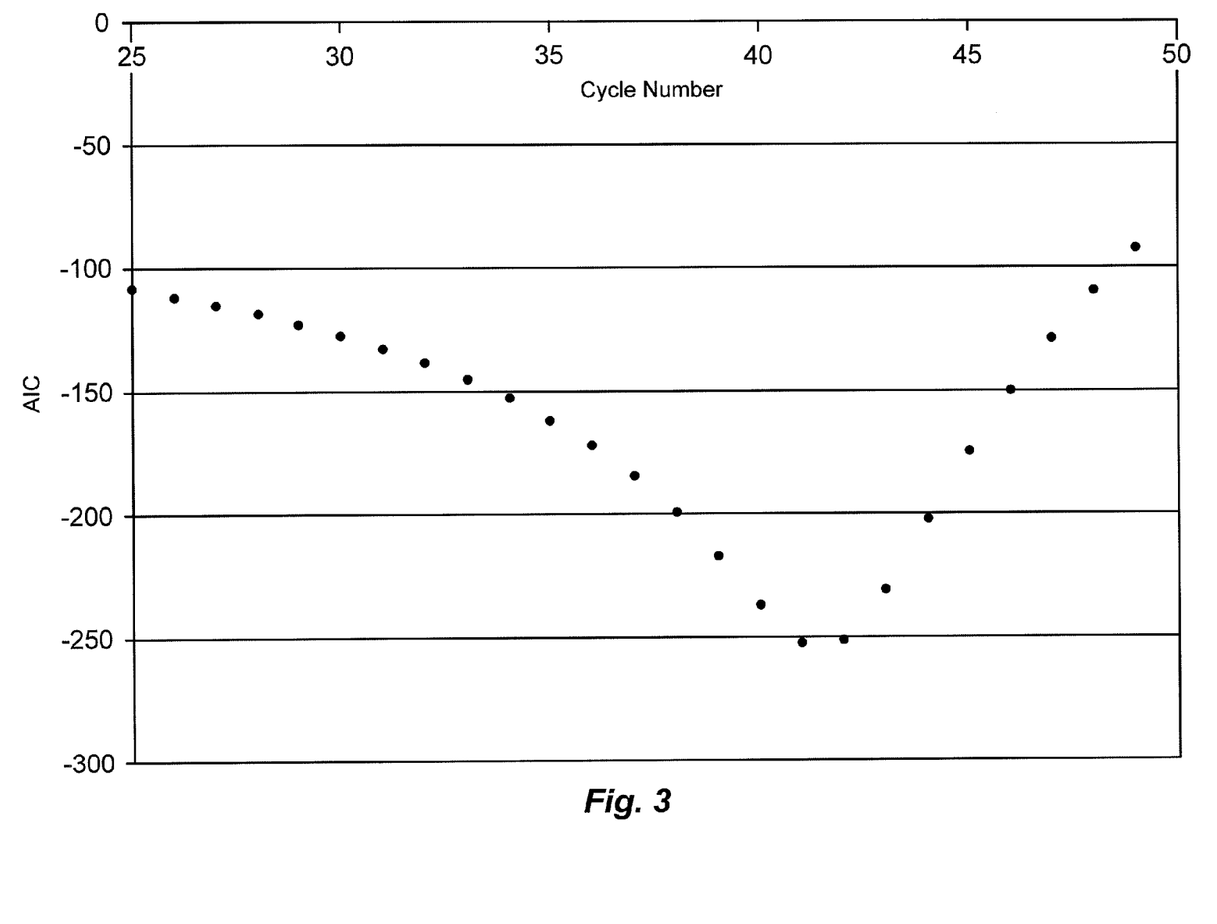
FIG. 3 illustrates a plot of the AIC v. cycle number, from cycle 25 to cycle 49 corresponding to the dotted line (parabolic shaped PCR curve) of FIG. 1.

Regression curve fits of Equation 1 were done for x* values from cycles 25 to cycle 49. For each curve fit, the AIC was calculated according to Equation 3. Shown in FIG. 3 is a plot of the AIC vs. cycle number, from cycle 25 to cycle 49 corresponding to the dashed curve shown in FIG. 1. The minimum AIC was found to occur at cycle number 41 and the coefficients for Equation 1 using x*=41 were found to be {a=0.002472; b=0.03460; c=0.25387}. These coefficients were determined by minimizing the function in Equation 2. This piecewise linear fit is accepted as the three conditions were satisfied, namely:

(1) c>0 and c/a=102.7, which is greater than the threshold 1.1.

(2) A quadratic fit of the raw data from cycle 41 to cycle 50 has and $R^2$ value of 0.99967, which is greater than the threshold of 0.90 or 0.99.

(3) A piecewise linear fit over all cycle numbers has an $R^2$ value of 0.9872, which is greater then the threshold of 0.85 or 0.95.

Using Equation 4 and the mean baseline subtracted value of the fluorescence=0.00533, the Ct is then calculated to be Ct=41.02.

It should be appreciated that the Ct determination processes, including the parabolic curve determination processes, may be implemented in computer code running on a processor of a computer system or other device or machine. The code includes instructions for controlling a processor to implement various aspects and steps of the Ct determination processes. The code is typically stored on a tangible medium such as a hard disk, RAM or portable medium such as a CD, DVD, memory stick, etc. Similarly, the processes may be implemented in a PCR device such as a thermocycler including a processor executing instructions stored in a memory unit integrated in or coupled with the processor. Code including such instructions may be downloaded to the PCR device memory unit over a network connection or direct connection to a code source or using a portable medium as is well known.

One skilled in the art should appreciate that the elbow determination processes of the present invention can be coded using a variety of programming languages such as C, C++, C#, Fortran, VisualBasic, etc., as well as applications such as Mathematica which provide pre-packaged routines, functions and procedures useful for data visualization and analysis. Another example of the latter is MATLAB®.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A computer-implemented method of determining a cycle threshold (Ct) value for a real-time polymerase chain reaction (PCR) data curve having a parabolic shape, the method comprising the steps, implemented in a computer system, of:

receiving a data set representing a PCR growth curve, the data set having a plurality of coordinate values (x,y), where x is a cycle number and y is an indicator of accumulated growth;

approximating the data set using a two segment piecewise linear function having a first linear segment ending at x* and a second linear segment beginning at x*, wherein the two segment piecewise linear function has the form:

$$f(x) = \begin{cases} ax + b, & x \le x^* \\ c(x - x^*) + ax^* + b, & x > x^*, \end{cases}$$

where a, b, and c are parameters for the approximation; determining, with the computer system:

a) whether an $R^2$ value of a quadratic fit to the data points beginning with x* to the end of the data set is above a predetermined threshold value of 0.90; and b) whether an $R^2$ value of the two segment piecewise fit over the data set is above a threshold value of 0.85; and c) whether the slope of the second segment is greater than the slope of the first segment if both slopes are greater than zero; and if a), b) and c) are true:

estimating, with the computer system, the Ct value of the data set using:

$$Ct = x^* + \frac{\underset{i=1...x^*}{\text{mean}} (y_i - ax_i - b)}{c - a};$$

and outputting the Ct value for display or further processing.

2. The method of claim 1, wherein approximating the data set includes minimizing an objective function at x*, wherein the objective function has the form:

$$E(a, b, c) = \frac{1}{2} \sum_{x_i \le x^*} (ax_i + b - y_i)^2 + \frac{1}{2} \sum_{x_i > x^*} (c(x_i - x^*) + ax^* + b - y_i)^2.$$

3. The method of claim 2, wherein x* is determined by applying the objective function to all data points from $x = n_0$ to n−1, where n is the number of cycles of the data set, $n_0$ is a predetermined starting cycle, and wherein x* is determined as the value of x which has a minimum Akaike Information Coefficient (AIC).

4. The method of claim 3, wherein the AIC is defined by the equation:

$$aic = n \cdot \ln\left(\frac{\|\hat{y} - y\|^2}{n}\right) + 2 \cdot m + \frac{2 \cdot m \cdot (m+1)}{n - m - 1},$$

where m is the number of degrees of the freedom of the two segment piecewise linear function, y is a data vector and $\hat{y}$ is a predicted model vector.

5. The method of claim 1, wherein for determining whether the $R^2$ value of a quadratic fit to the data points beginning with $x^*$ to the end of the data set is above the predetermined threshold value, the predetermined threshold value is 0.99.

6. The method of claim 1, wherein for determining whether the $R^2$ value of the two segment piecewise fit over substantially all the data set is above a threshold value, the threshold value is 0.95.

7. A non-transitory computer readable medium that stores code for controlling a processor to determine a cycle threshold (Ct) value for a real-time polymerase chain reaction (PCR) data curve having a parabolic shape, the code including instructions, which when executed by a processor, cause the processor to:

receive a data set representing a PCR growth curve, the data set having a plurality of coordinate values (x,y), where x is a cycle number and y is an indicator accumulated growth;

approximate the data set using a two segment piecewise linear function having a first linear segment ending at $x^*$ and a second linear segment beginning at $x^*$, wherein the two segment piecewise linear function has the form:

$$f(x) = \begin{cases} ax + b, & x \leq x^* \\ c(x - x^*) + ax^* + b, & x > x^*, \end{cases}$$

where a, b and c are parameters for the approximation;
determine:
a) whether an $R^2$ value of a quadratic fit to the data points beginning with $x^*$ to the end of the data set is above a threshold value of 0.90; and
b) whether an $R^2$ value of the two segment piecewise fit over the data set is above a threshold value of 0.85; and
c) whether the slope of the second segment is greater than the slope of the first segment if both slopes are greater than zero; and if a), b) and c) are true:
estimate the Ct value of the data set using:

$$Ct = x^* + \frac{\underset{i=1 \ldots x^*}{\text{mean}}(y_i - ax_i - b)}{c - a};$$

and
output the Ct value for display or further processing.

8. The computer readable medium of claim 7, wherein the instructions to approximate the data set include instructions to minimize an objective function at $x^*$, wherein the objective function has the form:

$$E(a, b, c) = \frac{1}{2} \sum_{x_i \leq x^*} (ax_i + b - y_i)^2 + \frac{1}{2} \sum_{x_i > x^*} (c(x_i - x^*) + ax^* + b - y_i)^2.$$

9. The computer readable medium of claim 8, wherein $x^*$ is determined by applying the objective function to all data points from $x = n_0$ to $n-1$, where n is the number of cycle of the data set, $n_0$ is a predetermined starting cycle, and wherein $x^*$ is determined as the value of x which has a minimum Akaike Information Coefficient (AIC).

10. The computer readable medium of claim 9, wherein the AIC is defined by the equation:

$$aic = n \cdot \ln\left(\frac{\|\hat{y} - y\|^2}{n}\right) + 2 \cdot m + \frac{2 \cdot m \cdot (m+1)}{n - m - 1},$$

where m is the number of degrees of the freedom of the two segment piecewise linear function, y is a data vector and $\hat{y}$ is a predicted model vector.

11. A real-time Polymerase Chain Reaction (PCR) system, comprising:

a PCR analysis module that generates a PCR data set representing a PCR growth curve, said data set including a plurality of data points each having a pair of coordinate values (x,y), wherein said data set includes data points in a region of interest which includes a cycle threshold (Ct) value, where x is a cycle number and y is an indicator of accumulated growth; and an intelligence module that includes a processor and that is adapted to process the PCR data set to determine the Ct value by:

approximating the data set using a two segment piecewise linear function having a first linear segment ending at $x^*$ and a second linear segment beginning at $x^*$, wherein the two segment piecewise linear function has the form:

$$f(x) = \begin{cases} ax + b, & x \leq x^* \\ c(x - x^*) + ax^* + b, & x > x^*, \end{cases}$$

where a, b, and c are parameters for the approximation;
determining whether the PCR growth curve has a parabolic shape by:
a) determining whether an $R^2$ value of a quadratic fit to the data points beginning with $x^*$ to the end of the data set is above a threshold value of 0.90; and
b) determining whether an $R^2$ value of the two segment piecewise fit over the data set is above a threshold value of 0.85; and
c) determining whether the slope of the second segment is greater than the slope of the first segment if both slopes are greater than zero; and if a), b) and c) are true:
estimating the Ct value of the data set using:

$$Ct = x^* + \frac{\underset{i=1 \ldots x^*}{\text{mean}}(y_i - ax_i - b)}{c - a};$$

and
outputting the Ct value for display or further processing.

12. The PCR system of claim 11, wherein approximating the data set includes minimizing an objective function at x*, wherein the objective function has the form:

$$E(a, b, c) = \frac{1}{2} \sum_{x_i \leq x^*} (ax_i + b - y_i)^2 + \frac{1}{2} \sum_{x_i > x^*} (c(x_i - x^*) + ax^* + b - y_i)^2.$$

13. The PCR system of claim 12, wherein x* is determined by applying the objective function to all data points from $x=n_0$ to n−1, where n is the number of cycles of the data set, $n_0$ is a predetermined starting cycle, and wherein x* is determined as the value of x which has a minimum Akaike Information Coefficient (AIC).

14. The PCR system of claim 13, wherein the AIC is defined by the equation:

$$aic = n \cdot \ln\left(\frac{\|\hat{y} - y\|^2}{n}\right) + 2 \cdot m + \frac{2 \cdot m \cdot (m+1)}{n - m - 1},$$

where m is the number of degrees of the freedom of the two segment piecewise linear function, y is a data vector and $\hat{y}$ is a predicted model vector.

* * * * *